United States Patent
Morgan et al.

(10) Patent No.: US 11,519,895 B2
(45) Date of Patent: Dec. 6, 2022

(54) IN SITU EVALUATION OF GASES AND LIQUIDS IN LOW PERMEABILITY RESERVOIRS

(71) Applicant: GAS SENSING TECHNOLOGY CORP., Laramie, WY (US)

(72) Inventors: Quentin Morgan, Laramie, WY (US); John Pope, Laramie, WY (US)

(73) Assignee: GAS SENSING TECHNOLOGY CORP., Laramie, WY (US)

( * ) Notice: Subject to any disclaimer, the term of this patent is extended or adjusted under 35 U.S.C. 154(b) by 726 days.

(21) Appl. No.: 16/319,654

(22) PCT Filed: Jul. 21, 2017

(86) PCT No.: PCT/US2017/043234
§ 371 (c)(1),
(2) Date: Jan. 22, 2019

(87) PCT Pub. No.: WO2018/017930
PCT Pub. Date: Jan. 25, 2018

(65) Prior Publication Data
US 2020/0124584 A1    Apr. 23, 2020

Related U.S. Application Data

(60) Provisional application No. 62/365,659, filed on Jul. 22, 2016.

(51) Int. Cl.
*G01N 33/24* (2006.01)
*E21B 49/08* (2006.01)
(Continued)

(52) U.S. Cl.
CPC .......... *G01N 33/24* (2013.01); *E21B 49/087* (2013.01); *G01N 21/27* (2013.01); *G01N 21/65* (2013.01);
(Continued)

(58) Field of Classification Search
CPC ...... G01N 33/241; G01N 33/24; G01N 21/65; G01N 21/27; E21B 43/11; E21B 43/112; E21B 47/0228; E21B 49/08
See application file for complete search history.

(56) References Cited

U.S. PATENT DOCUMENTS

2005/0178562 A1    8/2005   Livingstone
2008/0111064 A1    5/2008   Andrews et al.
(Continued)

FOREIGN PATENT DOCUMENTS

EP           0321198 A1    6/1989

OTHER PUBLICATIONS

SMEnergy Company, "Hydraulic Fracturing Process" https://www.youtube.com/watch?v=T_yfPcX1gG4, 2015 (Year: 2015).*
(Continued)

*Primary Examiner* — Maurice C Smith
(74) *Attorney, Agent, or Firm* — Pierson Intellectual Property LLC

(57) ABSTRACT

A method may include drilling a wellbore, the wellbore intersecting a shale formation at an interval of the shale formation and casing at least a portion of the wellbore. The method may also include perforating the casing at the interval to fluidly couple the interval and the wellbore, and liberating free and absorbed gas entrapped within the interval. In addition, the method may include solubilizing in the wellbore fluid the free and absorbed gas, forming a plume comprising solubilized gas, and determining an identity and amount of solubilized gas in the plume.

21 Claims, 9 Drawing Sheets

(51) Int. Cl.
  *G01N 21/27* (2006.01)
  *G01N 21/65* (2006.01)
  *G01N 21/85* (2006.01)
  *E21B 43/11* (2006.01)
  *E21B 47/06* (2012.01)
  *E21B 47/07* (2012.01)

(52) U.S. Cl.
  CPC .............. *G01N 21/85* (2013.01); *E21B 43/11* (2013.01); *E21B 47/06* (2013.01); *E21B 47/07* (2020.05); *G01N 2201/129* (2013.01)

(56) References Cited

U.S. PATENT DOCUMENTS

| | | | | |
|---|---|---|---|---|
| 2012/0043084 | A1* | 2/2012 | Jin | E21B 43/006 |
| | | | | 166/305.1 |
| 2012/0312530 | A1* | 12/2012 | Pope | G01V 8/02 |
| | | | | 250/269.1 |
| 2013/0146293 | A1* | 6/2013 | Zazovsky | E21B 43/26 |
| | | | | 166/308.1 |
| 2013/0152665 | A1 | 6/2013 | Dunlop et al. | |
| 2014/0138528 | A1 | 5/2014 | Pope et al. | |
| 2014/0300895 | A1 | 10/2014 | Pope et al. | |

OTHER PUBLICATIONS

CSIRO, "Unearthing coal seam gas", https://www.youtube.com/watch?v=FUD_26XuOqw, 2014 (Year: 2014).*

Haluszczak et al., "Geochemical evaluation of flowback brine from Marcellus gas wells in Pennsylvania, USA"; Applied Geochemistry 28 (2013) 55-61.

Charles Poth, "The Occurrence of Brine in Western Pennsylvania"; Pennsylvania Geological Survey Fourth Series Bulletin M 47, 1962.

International Search Report and Written Opinion issued in PCT/US2017/043234, dated Oct. 13, 2017, 10 pages.

* cited by examiner

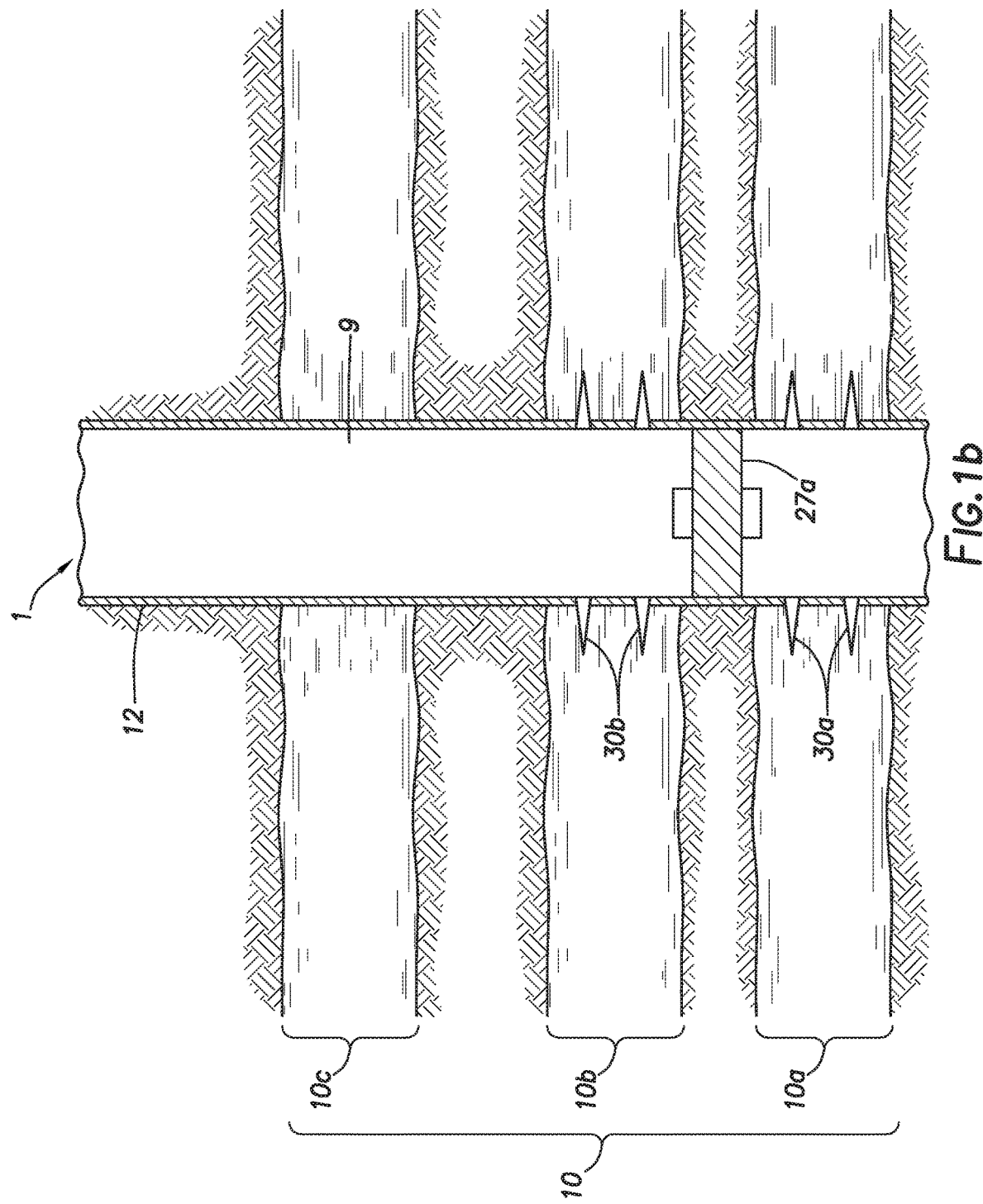

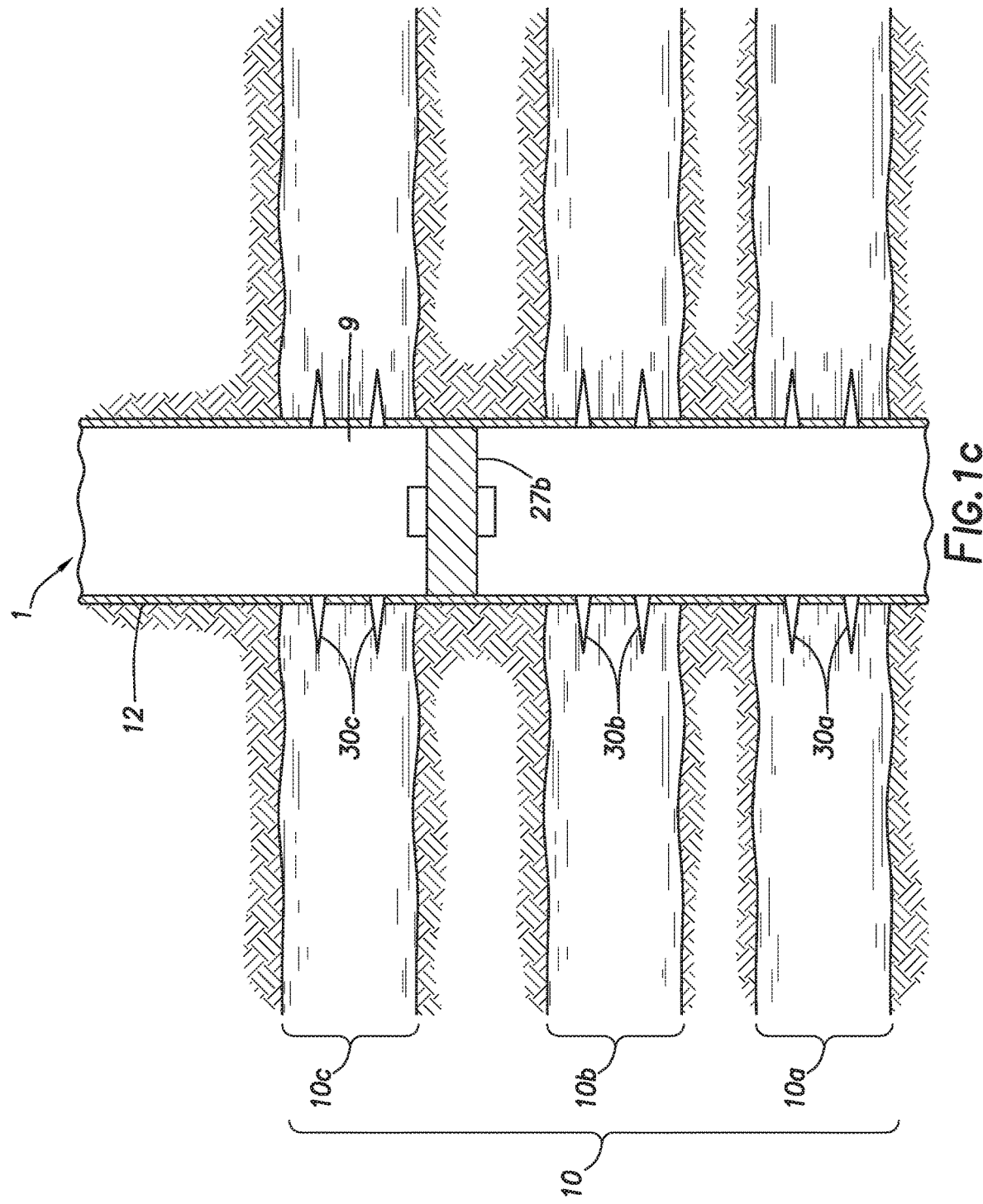

IN SITU EVALUATION OF GASES AND LIQUIDS IN LOW PERMEABILITY RESERVOIRS

CROSS-REFERENCE TO RELATED APPLICATIONS

This application is a National State Entry of PCT/US17/43234, filed Jul. 21, 2017; which itself claims priority from U.S. provisional application No. 62/365,659, filed Jul. 22, 2016. The entireties of both PCT/US17/43234 and U.S. 62/365,659 are incorporated herein by reference

FIELD

The present disclosure relates generally to methods and apparatuses for evaluating the location, identity and amount of gases and liquids contained within low permeability reservoirs.

BACKGROUND

The depositional processes that created certain shale reservoirs and the biogenic and thermogenic processes that reformed portions of the shale reservoirs into gas and liquids were heterogeneous. These heterogeneities in deposition and oil and gas evolution are compounded by the heterogeneous processes of faulting, uplift and fracturing that the shale reservoirs have undergone since deposition. As a result, shale reservoirs can have heterogeneity in hydrocarbon accumulation volumes, in the types and composition of hydrocarbons, and in the fracture networks contained therein. Types of gas and liquid available from shale reservoir intervals also vary, with some shale reservoir intervals yielding nearly pure methane gas, other shale reservoir intervals yielding natural gas liquids, others yielding oil, and others yielding combinations thereof.

One traditional method for quantification of gas and liquids in shale involves retrieval of a core sample of the shale, transportation of the core sample to a laboratory, and quantification of the amount of gas contained within the sample shale via gas desorption. This quantity is then analyzed to determine the shale gas content and compared to an adsorption isotherm of the same or similar shale in order to determine the relative amounts of free and absorbed gas and the critical desorption pressure of the absorbed phase to estimate the ultimate recovery of gas or liquids from the shale. Other reservoir evaluation technologies, such as seismic imaging and total organic carbon content may be used to reveal structural or geological characteristics of the reservoir, but do not directly analyze gas or liquids.

SUMMARY

The present disclosure provides for a method. The method includes drilling a wellbore, the wellbore intersecting a shale formation at an interval of the shale formation and casing at least a portion of the wellbore. The method also includes perforating the casing at the interval to fluidly couple the interval and the wellbore, and liberating free and absorbed gas entrapped within the interval. In addition, the method includes solubilizing in the wellbore fluid the free and absorbed gas, forming a plume comprising solubilized gas, and determining an identity and amount of solubilized gas in the plume.

The present disclosure provides for a method. The method includes drilling a first wellbore portion, the first wellbore portion intersecting a shale formation at a first interval of the shale formation. The method also includes casing at least the first wellbore portion to form a first cased wellbore portion, and perforating the first cased wellbore portion to fluidly couple the first interval and the wellbore. In addition, the method includes liberating free and absorbed gas entrapped within the first interval and solubilizing in wellbore fluid the free and absorbed gas, forming a first plume comprising solubilized gas. The method includes determining an identity and amount of solubilized gas in the first plume and drilling a second wellbore portion, the second wellbore portion intersecting the shale formation at a second interval of the shale formation. Also, the method includes casing at least the second wellbore portion to form a second cased wellbore portion and perforating the second cased wellbore portion to fluidly couple the second interval and the wellbore. In addition, the method includes liberating free and absorbed gas entrapped within the second interval and solubilizing in wellbore fluid the free and absorbed gas, forming a second plume comprising solubilized gas. The method includes determining an identity and amount of solubilized gas in the second plume.

The present disclosure provides for a method. The method includes drilling a wellbore the wellbore intersecting a shale formation at a first interval and a second interval of the shale formation, wherein the first interval is located further from a surface than the second wellbore. The method also includes casing the wellbore to form a cased wellbore and perforating the cased wellbore to fluidly couple the first interval and the wellbore. In addition, the method includes liberating free and absorbed gas entrapped within the first interval and solubilizing in wellbore fluid the free and absorbed gas, forming a first plume comprising solubilized gas. The method also includes determining an identity and amount of solubilized gas in the first plume and reinjecting the solubilized gas from the first plume into the first interval. In addition, the method includes isolating the first interval from the second interval and perforating the cased wellbore to fluidly couple the second interval and the wellbore. The method includes liberating free and absorbed gas entrapped within the second interval and solubilizing in wellbore fluid the free and absorbed gas, forming a second plume comprising solubilized gas. The method also includes determining an identity and amount of solubilized gas in the second plume.

BRIEF DESCRIPTION OF DRAWINGS

The present disclosure may be understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIGS. 1A, 1B, and 1C are schematic views of a wellbore in accordance with certain embodiments of the present disclosure.

DETAILED DESCRIPTION

Figure 1A:
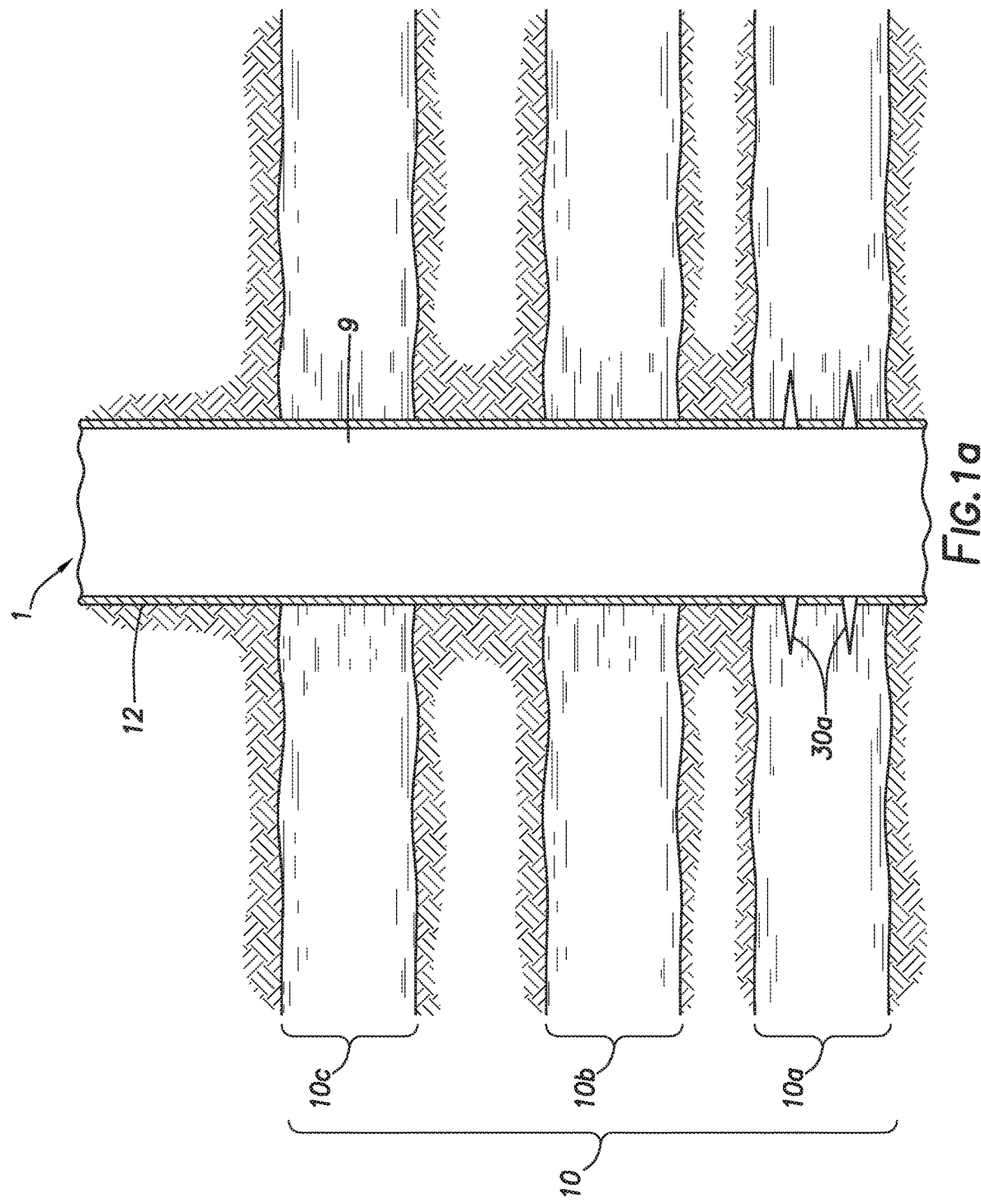

A detailed description will now be provided. The following disclosure includes specific embodiments, versions and examples, but the disclosure is not limited to these embodiments, versions or examples, which are included to enable a person having ordinary skill in the art to make and use the disclosure when the information in this application is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Certain embodiments of the present disclosure relate to a method for determining a location, identity and an amount of a gas or a liquid contained in one or more intervals of a low permeability formation. Examples of low permeability formations include, but are not limited to, shale, coal, tightly-packed sand and clays. "Low permeability formation" refers to a formation that has a matrix permeability of less than 1,000 microDarcy (equivalent to 1 milliDarcy). For purposes of this disclosure, an "interval" of a low permeability formation is a portion of the low permeability formation intersected by a wellbore. A well bore may intersect one or more intervals. In certain embodiments, as described hereinbelow, the intervals of the low permeability formation intersected by the well may be physically isolated from one another, The gas may be methane, carbon dioxide, nitrogen, or a natural gas liquid such as ethane, propane, butane, or combinations thereof. Liquids may contain these same gases in the solubilized state and in some embodiments may include higher hydrocarbon fractions in the liquid state. As used herein, "liquid" refers to any hydrocarbon with more than one carbon atom. As also used herein "gas or liquid" includes combinations of gases and liquids. A low permeability formation may include oil and/or gas containing rocks, shales, clays, tight sands, mudstones, and tight carbonates.

In some embodiments of the present disclosure, the method for determining location, identity, and amount of a gas or liquid contained in one or more intervals of a low permeability formation may include extracting fluids from an interval and measuring the fluids within the wellbore. In certain embodiments of the present disclosure, the wellbore may contain a wellbore fluid, such as water. The method for determining location, identity, and amount of a gas or liquid may include perforating the casing of the wellbore to establish fluid communication between the wellbore and the interval by forming a perforated interval. Gases and liquids liberated from the perforated interval are expelled into the wellbore. Gases may be solubilized by the wellbore Liquids expelled into the wellbore may form a mixture with the wellbore fluid. In certain embodiments, the liquid/wellbore fluid mixture may be an emulsion. The region within the wellbore containing both wellbore fluid and any solubilized gases and/or oil liberated from the perforated interval is known as a plume. The method may further include measuring the concentration of gases and/or liquids in the plume. In some embodiments, the method may further include pumping the contents of the plume into the perforated interval, isolating a second interval, perforating the casing of the wellbore to establish fluid communication between the wellbore and the second interval by forming a second perforated interval, allowing the gases and liquids liberated from the second perforated interval to be expelled into the wellbore and be solubilized or mixed with the wellbore fluid to create a plume, and measuring the concentration of gases and/or liquids in the plume.

FIGS. 1A, 1B, 1C depict low permeability formation 10 intersected by wellbore 1 at intervals 10*a*, 10*b*, and 10*c*. FIGS. 1A, 1B, 1C are consistent with the results of the step of perforating the casing of the wellbore to establish fluid communication between the wellbore and the interval by forming a perforated interval. While FIG. 1 depicts three intervals, one skilled in the art will understand that wellbore 1 may intersect low permeability formation 10 at more or less than three intervals. In certain embodiments, intervals 10*a*, 10*b*, and 10*c* are encased. In other embodiments, such as the embodiment shown in FIG. 1, intervals 10*a*, 10*b*, and 10*c* may be lined or "cased" by casing 12. In yet other embodiments, some of intervals 10*a*, 10*b*, and 10*c* may be cased and others uncased. Casing 12 may include a single casing string or multiple casing strings mechanically coupled. Casing 12 may be cemented in wellbore 1, such that any annulus between casing 12 and wellbore 1 is sealed with cement. While FIG. 1 depicts a vertical wellbore, one of skill in the art with the benefit of this disclosure will appreciate that wellbore 1 may include vertical sections, deviated sections, and lateral sections. Perforation of wellbore 1 may be performed in any of the vertical sections, deviated sections, or lateral sections of wellbore 1.

Wellbore 1 may be partially or completely filled with wellbore fluid 9. Wellbore fluid 9 may include fluids from one or more layers of geological strata, including low permeability, formation 10, or may include residual fluids from drilling and completion operations. Wellbore fluid 9 may include water. In some embodiments, wellbore fluid 9 may include water added from a surface source. In some embodiments, one or more intervals 10*a*, 10*b*, and 10*c* are partially or wholly saturated with water. In some embodiments, one or more intervals 10*a*, 10*b*, and 10*c* are dry or partially dry.

As depicted in FIGS. 1A, 1B, 1C, wellbore 1 may be drilled to at least the depth of low permeability formation 10. At least a portion of wellbore 1 may be cased by installing casing 12. In some embodiments, the entirety of wellbore 1 may be cased. In other embodiment, none of wellbore 1 is cased. The step of perforating casing 12 of the wellbore to establish fluid communication between wellbore 1 and the interval by forming a perforated interval may be performed by perforating casing 12 in first interval 10*a* and forming perforation tunnels 30*a* in first interval 10*a* to fluidly couple first interval 10*a* of low permeability formation 10 to wellbore 1. The step of perforating may liberate free and absorbed gas entrapped within first interval 10*a*. As used herein, "free gas" refers to gas contained within reservoir 10 that is not absorbed into the shale. As used herein, "absorbed gas" refers to gas contained within reservoir 10 that are absorbed in the shale. The step of perforating may also liberate liquids entrapped within first interval 10a. At least a portion of the liberated gas or liquid may be expelled from within first interval 10a into wellbore 1. The liberated gas may be solubilized in wellbore fluid 9 contained within wellbore forming a first plume. Liberated liquids may be mixed with wellbore fluid 9 and be included in the first plume.

In certain embodiments, perforating may be performed using one or more perforating guns. For example and without limitation, shaped charges within a perforating gun may be detonated to propel a focused pressure wave outward of each shaped charge and toward low permeability formation 10. Each pressure wave, along with the mass of the perforating liner, may provide a force that forms a hole through casing 12 and cement, extends into low permeability formation 10, and pulverizes portions of low permeability formation 10 to form perforation tunnels 30a, which may be cylindrical. Without being bound by theory, the pulverization may at least partially destroy the connected and isolated pore network present within the inorganic rock matrix and organic matter in low permeability formation 10. Destruction of the connected and isolated pore network present within the inorganic rock matrix and organic matter in low permeability formation 10 may release some or all of the absorbed and free gas and liquid occupying the pulverized portion of low permeability formation 10, and may release free water present in low permeability formation 10. Back surging created by underbalanced perforating or by pressure of the liberated gas may cause the gas, liquid, and low permeability formation 10 formation water to be expelled into wellbore 1. The liberated gas and liquid may then migrate up the borehole of wellbore 1 under buoyancy effects, until the liberated gas is solubilized by and liquids are mixed into well bore fluid 9 present in wellbore 1. The upward migration of gas bubbles and liquid may draw formation water up wellbore 1, creating a region in wellbore 1 extending a certain distance uphole from perforation tunnels 30a with a chemistry that differs from the surrounding wellbore fluid, which is referred to herein as the "plume." The plume contains the solubilized gas and liquid and may have an altered salinity.

Without being bound by theory, it is believed that the plume attains a certain height with concentration profiles of the gas and liquid becoming stable after the liberated gas has been solubilized and the liquid mixed with the formation water. Thereafter, the plume disperses, driven by diffusion-driven exchange of solubilized gases, liquid and salt ions between the plume and the wellbore fluid 9 above.

In certain embodiments, the location, identity, and amount of the solubilized gas and/or liquid in the first plume may be determined. "Location" refers to interval of the formation from which the gases and/or liquid were expelled. As used herein, "identity" of the solubilized gas and/or liquid refers to the particular molecule(s) of gas or liquid. In some embodiments, the identity of the solubilized gas may be methane.

Determining the identity and amount of the solubilized gas and liquid in the first plume may include, at multiple discrete depths in the first plume, providing incident radiation from a radiation source to the solubilized gas and liquid within the first plume. Interaction of the incident radiation with the solubilized gas and liquid within the first plume forms characteristic radiation from the solubilized gas and liquid within the first plume. For example and without limitation, if the detected gas present in the first plume is methane, the incident radiation may interact with the methane, causing the methane to emit, scatter, or reflect characteristic radiation. Determining the identity and amount of the solubilized gas and liquid in the first plume may further include, for each of the multiple discrete depths, detecting the characteristic radiation with a radiation detector. The radiation detector may form a signal representative of the characteristic radiation.

In some embodiments, the radiation source and the radiation detector are separate devices. In some embodiments, the radiation source and the radiation detector are each parts of the same sensor assembly. For example and without limitation, the radiation source and the radiation detector may each be a part of a spectrometer. The spectrometer may be an optical spectrometer or a mass spectrometer, for example. In certain embodiments, the optical spectrometer is a Raman spectrometer, a near IR spectrometer, a IR spectrometer, a UV/Vis spectrometer or fluorimeter. In some embodiments, the radiation detector is a membrane-coated semiconductor sensor or a charge coupled device (CCD). In some embodiments, determining the identity of the solubilized gas and liquid in the first plume is performed using a sensor, for example, an optical spectrometer, in tandem with a sample collector, such as a formation tester. In some embodiments, determining the identity and amount of the solubilized gas and liquid hydrocarbons thereof in the first plume is performed using a transducer or sensor that provides a signal in response to the concentration of gas or liquid. In certain embodiments, the sensor assembly may determine the partial pressure of the gas. One skilled in the art with the benefit of this disclosure will recognize that reference to a partial pressure of a gas dissolved in a fluid is related to the amount of that gas dissolved in that fluid, and would be in equilibrium with a vapor phase in contact with that fluid. As used herein "partial pressure of gas in fluid" encompasses, but is not limited to, concentration, effective density, quantity, potential volume, potential pressure, and amount.

Figure 5:
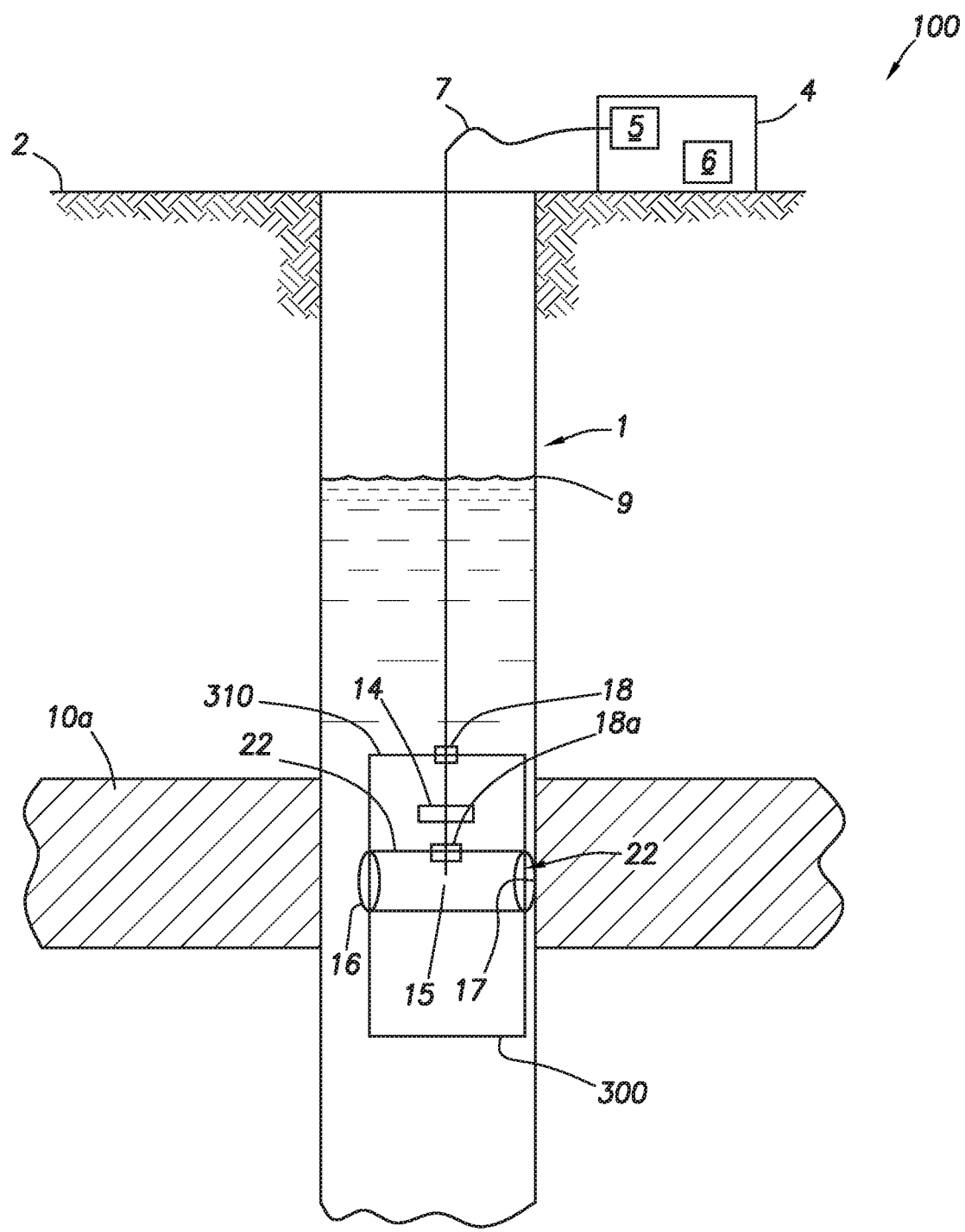
FIG. 5 depicts a sensory assembly in accordance with certain embodiments of the present disclosure.

FIG. 5 depicts spectrometer 100 deployed in wellbore 1 in a manner consistent with certain embodiments of the present disclosure. Spectrometer 100 includes surface portion 4, located at surface 2 and downhole portion 310, located within wellbore 1. Surface portion 4 may include radiation source 5 for producing incident radiation to transmit down wellbore 1 to interface with the plume within wellbore fluid 9. Surface portion 4 may further include radiation detector 6. Surface portion 4 may be connected to downhole portion 310 by optical pathway 7.

In some embodiments, optical pathway 7 is an optical fiber. Optical pathway 7 may include a guide wire and optical fibers. For example and without limitation, optical pathway 7 may be a bundle of optical fibers, including a center fiber that transmits the incident radiation from radiation source 5, and one or more additional fibers that transmit the characteristic radiation to radiation detector 6. In some embodiments, optical pathway 7 includes a lens for optically coupling with the gas or liquid.

Optical pathway 7 may extend into wellbore 1 to mechanically and optically connect surface portion 4 to downhole portion 310. In certain embodiments, downhole portion 310 includes housing 300. In some embodiments, housing 300 is a steel housing. In certain embodiments, downhole portion 310 includes additional sensors for pressure, temperature, and conductivity, which may be incorporated into an endcap of housing 300.

Optical pathway 7 may pass into housing 300 through high-pressure feed-through jacket 18. High-pressure feed-through jacket 18 may allow optical pathway 7 to enter housing 300 without subjecting elements of downhole portion 310 within housing 300 to the conditions within the wellbore, such as high pressure, particles and fluids. Housing 300 may protect filter 14 or other instrumentation enclosed by housing 300. Optical pathway 7 may extend out of housing 300 through inlet high-pressure feed-through jacket 18a to optically couple with gas thereof at tip 15. Tip 15 of optical pathway may supply the incident radiation from radiation source 5 and collect the characteristic radiation. Tip 15 may be a polished tip or fused tip, for example. As depicted in FIG. 5, housing 300 includes sample interface 22, including inlet 16 and outlet 17, for fluidly coupling wellbore fluid 9 with tip 15. In operation, wellbore fluid 9 flows into inlet 16 when housing 300 is positioned within wellbore and flows around tip 15, interacting with the incident radiation from radiation source 5.

The incident radiation from radiation source 5 may be transmitted through at least one optical pathway 7. The gas or liquid in the plume may interact with the incident radiation, forming a characteristic radiation for the gas or liquid. The characteristic radiation may be transmitted by optical pathway 7 to radiation detector 6 located within surface portion 4 at surface 2.

Figure 6:
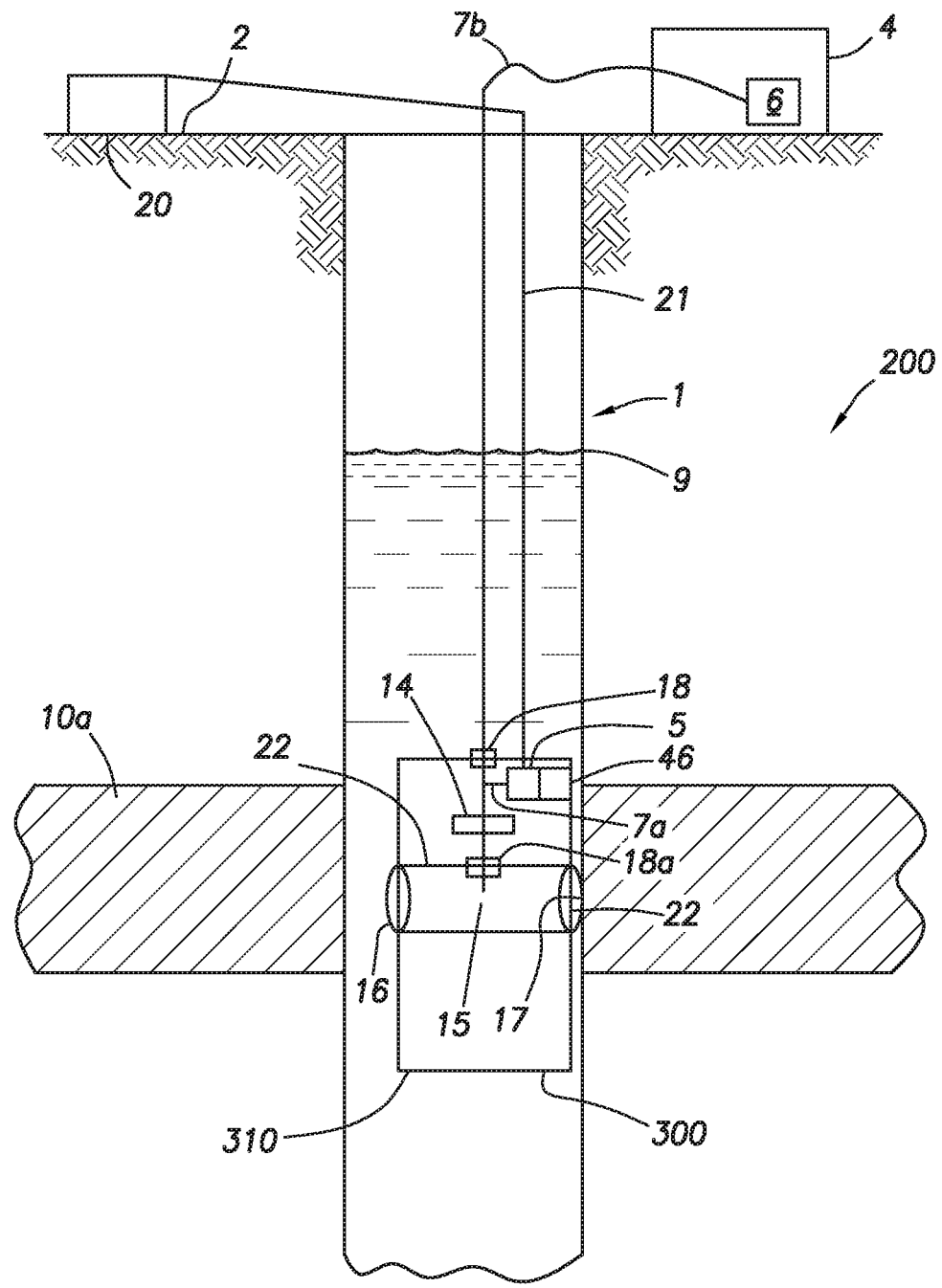
FIG. 6 depicts a sensory assembly in accordance with certain embodiments of the present disclosure.

In the embodiment shown in FIG. 6, spectrometer 200 includes radiation detector 6 within upper portion 4 and radiation source 5 within downhole portion 310. Without being bound by theory, locating radiation source 5 in downhole portion 310 may reduce effects of long distance transmission of the incident radiation. Radiation source 5 may be positioned within wellbore 1 by lowering radiation source 5 with guide wire 21 to a depth. The depth may be controlled by guide controller 20 at surface 2. In some embodiments, guide wire 21 is a wireline having an insulated electrical conductor inside a braided inner and outer armor. In some embodiments, guide wire 21 is a slickline having a solid smooth non-braided metal construction. In some embodiments, guide wire 21 is coiled tubing, drill stem, or another type of guide. Guide wire 21 may be provided for positioning housing 300 down the well and may also transmit signals to a data recorder or other processor at surface 2. In some embodiments, a signal or data storage device is located in housing 300. In some embodiments, guide wire 21 provides electrical power to instrumentation located in housing 300, or a battery may be located in housing 300.

The incident radiation from radiation source 5 may be transmitted by way of at least one optical pathway 7a to interact with gas or liquid, forming characteristic radiation. The characteristic radiation may then be transmitted by optical pathway 7h to radiation detector 6 located within surface portion 4 at surface 2. In some embodiments, radiation source 5 is electrically powered by battery 46 or by guide wire 21 with electrical conductors (not shown).

Figure 7:
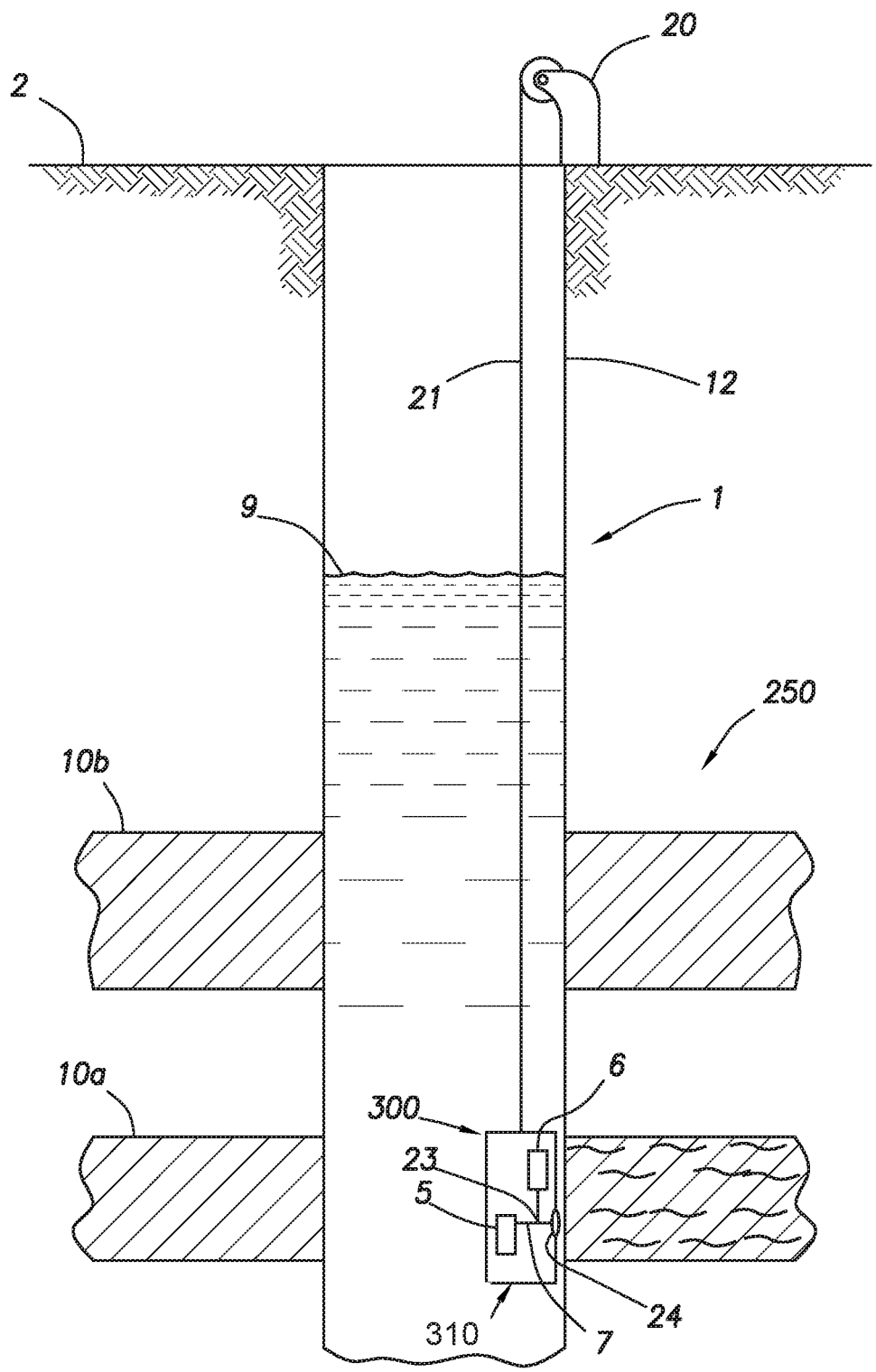
FIG. 7 depicts a sensory assembly in accordance with certain embodiments of the present disclosure.

In the embodiment shown in FIG. 7, spectrometer 250 includes radiation source 5 and radiation detector 6 located within downhole portion 310. Radiation source 5 provides the incident radiation through optical pathway 7, which may or may not be an optical fiber. The incident radiation may be directed to beam splitter 23 and through window 24 to interact with the gas or liquid, forming characteristic radiation. The characteristic radiation may then be transmitted through window 24, through beam splitter 23, and to radiation detector 6.

By directing the incident radiation through window 24 (or tip 15, as shown in FIGS. 5 and 6), the incident radiation interacts with the gas or liquid within the plume outside of the sensory assembly.

In some embodiments, radiation source 5 is located outside of casing 12, and the incident radiation is guided from radiation source 5 into casing 12, as is shown in FIG. 5. In some embodiments, radiation source 5 is located inside casing 12, as is shown in FIGS. 6 and 7.

In some embodiments, radiation detector 6 is located outside of casing 12, and the characteristic radiation is guided from within casing 12 to radiation detector 6, as is shown in FIGS. 5 and 6. In some embodiments, radiation detector 6 is located inside of casing 12, as is shown in FIG. 8.

In certain embodiments, a controller (not shown) may be used to input operating parameters for spectrometers 100, 200, 250 and package spectral data for delivery to an uphole computer. Uphole computer may include a non-transitory, tangible computer-readable memory medium. The non-transitory, tangible computer-readable memory medium may include computer program instructions to process the signals from radiation detector 6. For example and without limitation, the non-transitory, tangible computer-readable memory medium may include computer program instructions that cause the computer to use data in the signals to solve equations (I)-(V) disclosed herein below. In certain embodiments, the uphole computer and computer program instructions may allow a user to set the operating parameters for spectrometers 100, 200, 250 and graphically display data delivered from the controller, for example, on a graphical user interface. In some embodiments, a calibration file may be created by correlating response and spectra of dissolved gas to known concentrations of dissolved gas and liquids to known concentration of liquids. The calibration file may be stored on the non-transitory, tangible computer-readable memory medium, and the non-transitory, tangible computer-readable memory medium may include computer program instructions that cause the computer to use the calibration file to predict gas concentration from the spectra delivered uphole by radiation detector 6.

Determining the location, identity, and amount of the solubilized gas or liquid in the first plume may include processing each signal representative of the characteristic radiation to determine an identity and amount of the solubilized gas or mixed liquid at the multiple discrete depths within the first plume. In some embodiments, processing each signal to determine the location, identity, and amount of the solubilized gas or mixed liquid at the multiple discrete depths within the first plume includes correlating each signal with a calibration function that is a function of signal versus amount of solubilized gas or mixed liquid. The calibration function may define a calibration curve. By correlating the signals measured for a series of samples with the concentrations of one or more gases dissolved or liquids mixed in the samples, a calibration between signal and concentration may be determined.

For example and without limitation, calibration of a Raman spectrometer to allow for conversion between a Raman spectrum and a concentration of gas may include preparing samples of the gas in equilibrium with water at various pressures. Raman spectra of the samples may be taken. The pressures of the samples may be correlated with partial pressures of unknown samples. The concentration of the gas in each sample may be calculated by Henry's law, using an appropriate Henry's law constant for the given conditions (i.e., temperature, salinity and gas partial pressure), or by another method that indicates the solubility of the gas in water. The gas concentration may then be correlated with the intensity of the gas peak in the Raman spectra of the sample. Using this technique, concentration of the gas may be calculated by measuring the Raman spectrum of an unknown sample.

In some embodiments, calibration of a Raman spectrometer to allow for conversion between a Raman spectrum and a concentration of liquid may include preparing samples of the liquid at various concentrations in water. In certain embodiments, such as where the liquid and water are highly miscible, limited or no treatment may be required to form a homogenous mixture of water and liquid. Limited treatment may include, but not be limited to a shaker or mixer. Where the liquid and water are less miscible, no or limited treatment may form a suspension to be used for calibration of the Raman spectrometer. A non-limiting example of a sample of liquid and water that may necessitate only limited or no treatment may be a water/light oil/cyclohexane sample. In other embodiments, where liquids have limited miscibility in water, other methods may be used to prepare samples at various concentrations. For example, the liquid/water sample may be subjected to high speed mixing or sonication. Alternatively, data on the sample may be collected over time and the signals averaged as different phases pass through the focal point. In yet another alternative, the CCD may be exposed to the different phases over time and an average taken. In still other alternative embodiments, calibrations for each phase may be taken independently. In yet other alternate embodiments, the sample may be prepared in a mixed state such that partitioning is obtained in the calibration. In these embodiments, a cell is charged containing water and liquid with gas at a predefined partial pressure. The Raman spectrometer is used to determine the amount of water in the water phase and the liquid present in the liquid phase. The liquid/water concentrations may then be altered and the process repeated.

In some embodiments, a variation in the identity and amount of the gas or liquid within a plume by depth, by time, or by depth and by time may be determined. As described above, determining an amount of gas or liquid within a plume may be performed at multiple discrete depths. The amounts of the gas or liquid within a plume may then be plotted as a function of depth. As depth is increased, the measured concentration may increase to a certain maximum at a point across the perforations and diminishes to zero or below the perforations. The asymmetry in the gas or liquid concentration profile may be indicative of gas bubbles and liquid entering wellbore 1 via perforation tunnels 30a and migrating upwards under buoyancy effects until being solubilized by wellbore fluid 9. By integrating measured concentrations of solubilized gas or liquid over the height of the plume, a total mole amount of each gas and/or liquid present in the plume may be determined. In the absence of physicochemical processes, repeated concentration measurements of the solubilized gas or liquid over the height of the plume may result in the same computed total mole amount of each gas solubilized or liquid mixed in the plume.

The method may include processing the total amount of the solubilized gas or mixed liquid within the first plume to determine a concentration of the gas, both free and absorbed or liquid. Such processing of free and absorbed gas may be performed in accordance with one or more of equations (I)-(V), as disclosed herein.

In some embodiments, equations (I)-(V), as set forth below may be used to determine the total free and absorbed gas content from concentration measurements in the plume. While equations (I)-(V) are discussed with reference to the gas, methane, one skilled in the art will understand that the same method may be applied to other gases identified in the plume.

The total mole amount Ni of a particular gas species, such as methane or carbon dioxide, or liquid hydrocarbon fraction, such as a C7 hydrocarbon, detected in the plume during an initial logging run is determined by integrating measurements of the concentration of the particular gas species or liquid hydrocarbon fraction at discrete depths in the plume across the entire height of the plume. As used herein, a "logging run" refers to a single pass of an instrument through the entire height of the plume for detection of characteristic radiation. In some embodiments, logging speed can be adjusted to capture data that describes movement of gases through the wellbore, and increase accuracy of determined gas content of the perforated interval. As used herein "logging speed" refers to a rate at which an instrument takes measurements while passing through the plume for detection of characteristic radiation. The total mole amount Ni of a particular gas species or liquid fraction detected in the plume during the initial logging run may be determined in accordance with equation (I):

$$N_i = A \sum_{x=1}^{Y} \frac{(C_{x+1} + C_x)(D_{x+1} - D_x)}{2} \quad (I)$$

In equation (I), D is measurement depth; C is the measured concentration of the particular gas species or liquid fraction; x is sample number; Y is the total number of discrete samples acquired in the plume; and A is the cross section area of the wellbore.

The total mole amount of a particular gas species or liquid fraction released at the time of perforating N0 may be determined in accordance with equation (II):

$$N_0 = N_i - \frac{(N_l - N_i)}{dt} \Delta T \quad (II)$$

In equation (II), N1 is the gas or liquid fraction mole amount computed from the final logging run through the plume; dt is the time duration between the first and final logging run through the plume; and $\Delta T$ is the time duration between the instance of perforating and the first logging run through the plume, The total mole amount of a particular gas species released at the time of perforating N0 is converted to a volume Vg in cubic feet of that gas at standard conditions using the universal gas law, equation (III) as follows:

$$V_g = \frac{A * N_0 * R * T_s}{P_s} \quad (III)$$

In equation (III), A is a constant equal to 0.035 ft3/liter; R is the universal gas constant, 0.08206 L·atm-1·mol-1·K1, Ts is standard temperature, 288.71 K; and Ps is standard pressure, 1 atmosphere.

Vs is equated to the free and absorbed gas content Gc of the particular gas species in the perforated low permeability interval in accordance with equation (IV):

$$G_c = \frac{B * V_g}{\rho * V_t} \quad \text{(IV)}$$

In equation (IV), Gc is the amount in ft3/short ton of the free and absorbed gas species within the interval; B is a constant equal to 2000 lb/short ton; ρ is the density in lb/ft3 of the low permeability interval; and Vp is the total volume of rock pulverized by the perforating guns in ft3. Vp is determined in accordance with equation (V):

$$V_p = H * spf * \frac{\pi}{4} d^2 * L \quad \text{(V)}$$

In equation (V), H is the total length in feet of a perforating gun used in the perforating; spf is the shot density used in the perforating; d is the perforation tunnel diameter in feet; and L is the perforation tunnel length in feet, equal to penetration length less the thickness of the casing and cement sheath. Sample data that may be used in equation (V) is shown below in Table 1.

The total gas free and absorbed gas content stored in the low permeability reservoir at the perforated interval will equate to the sum of the individual Gc values determined for every gas species detected in the plume.

$$O_c = \frac{B * V_l}{\rho * V_p} \quad \text{(VII)}$$

In equation (VII), Oc is the amount in ft3/short ton of the liquid hydrocarbon fraction within the interval; B is a constant equal to 2000 lb/short ton; ρ is the density in lb/ft3 of the low permeability interval; and Vp is the total volume of rock pulverized by the perforating guns in ft3. Vp is determined in accordance with equation (V).

The total liquid content stored in the low permeability reservoir at the perforated interval will equate to the sum of the individual Oc values determined for every liquid hydrocarbon fraction detected in the plume.

In some embodiments, the pressure, conductivity, temperature, or combinations thereof may be measured at some or each of the multiple discrete depths within the plume. Pressure, conductivity, and temperature may be measured by methods known to those of ordinary skill in the art. For example and without limitation, pressure may be measured with a pressure sensor, conductivity may be measured with a conductivity sensor, and temperature may be measured with a temperature sensor. In some embodiments, the method includes measuring salinity at some or each of the multiple discrete depths within a plume using a salinity sensor. In certain embodiments of the method, salinity of the

TABLE 1

| O.D. (IN.) | CHARGE TYPE | SHOT DENSITY (SPF) DRY OR FLUID | PHASING | CHARGE CODE | CHARGE P/N | EXP WEIGHT (G.) | CASING O.D. (IN.) | ENTRY HOLE (IN.) | PEN. (IN.) | PEN. NORM @ 5000 PSI (IN.) | TEMP 1 HR |
|---|---|---|---|---|---|---|---|---|---|---|---|
| 1¹¹/₁₆ | BH | 4F/6F | 0° | — | STP-1687-301BE | 10.8 | 5½ | 0.48 | 10.54 | 10.54 | 310° F. |
| 1¹¹/₁₆ | DP | 4F | 0°/180° | — | BWC-1687-301 | 10 | 5½ | 0.4 | 8.06 | 8.06 | 310° F. |
| 1¹¹/₁₆ | DP | 4F | 0°/180° | — | FWC-1687-301 | 10 | 5½ | 0.4 | 8.06 | 8.06 | 310° F. |
| 1¹¹/₁₆ | DP | 4F | 0°/90°/180° | — | LNK-1687-301 | 10 | 5½ | 0.4 | 8.06 | 8.06 | 310° F. |
| 1¹¹/₁₆ | BH | 4D/6D | 0°/60°/90°/180° | 38 | RTG-1687-401BH | 3.2 | 2⅞ | 0.37 | 2.7 | 3.5 | 400° F. |
| 1¹¹/₁₆ | SDP | 4D/6D | 0° | 38 | SDP-1687-402NT3 | 3.3 | 2⅞ | 0.16 | 12.2 | 15.13 | 400° F. |
| 1¹¹/₁₆ | SDP | 4D/6D | 60°/90°/180° | 38 | SDP-1687-402NT3 | 3.3 | 2⅞ | 0.16 | 10.56 | 12.05 | 400° F. |
| 1¹¹/₁₆ | BH | 4D/6D | 0°/60°/90°/180° | 38 | RTG-1687-301BH | 3.3 | 4½ | 0.37 | 3.29 | 3.29 | 330° F. |
| 1¹¹/₁₆ | DP | 4F/6F | 0° | — | STP-1687-301T | 7.5 | 4½ | 0.26 | 17.88 | 17.88 | 310° F. |
| 1¹¹/₁₆ | BH | 4F/6F | 0°/60°/40° | — | STP-1687-301NB | 8.3 | 5½ | 0.48 | 10.54 | 10.54 | 310° F. |

The total mole amount of a particular liquid fraction released at the time of perforating $N_O$ is converted to a volume V1 in ft3 in accordance with equation (VI):

$$V_l = \frac{C * N_o * MW}{\rho} \quad \text{(VI)}$$

In equation (VI), C is a constant equal to 0.00003531 ft3/cm3; MW is the molecular weight in grams per mole of the liquid hydrocarbon fraction and ρ is the density in grams/cm3 of the liquid hydrocarbon fraction.

VI is equated to the total liquid Oc of the particular hydrocarbon fraction in the perforated interval in accordance with equation (VII):

plume is determined by analyzing distortion in the water O—H stretch Raman peak present in the acquired spectra. The O—H stretch Raman peak is a composite of both symmetric and asymmetric stretch modes. The height ratio of the individual symmetric and asymmetric modes may vary with increasing salinity.

In some embodiments, after perforating casing 12, wellbore fluid 9 may enter perforation tunnels 30a and contact the exposed surfaces within low permeability formation 10. Without being bound by theory, contact of wellbore fluid 9 with exposed surfaces may result in one or more physicochemical interactions between wellbore fluid 9 and the surfaces, including spontaneous imbibition of wellbore fluid 9 into the low permeability formation. Such physicochemical interactions may cause wellbore fluid 9 to be drawn into the exposed low permeability formation, and may establish a countercurrent of additional gas and/or liquid into wellbore which may be driven by diffusion gradients. In some embodiments, if the rate at which wellbore fluid 9 is drawn through into perforation tunnels 30a and into the low permeability formation exceeds the countercurrent flow potential of additional gas and/or liquid into wellbore 1, then the total mole amount of gas or liquid contained in the plume created by the perforating will diminish over time. In other embodiments, if the rate at which wellbore fluid 9 is drawn through into perforation tunnels 30a and into the low permeability formation is less than the countercurrent flow potential of additional gas or liquid into wellbore 1, then the total mole amount of gas or liquid contained in the plume created by the perforating will increase over time. In such embodiments where the wellbore fluid 9 enters perforation tunnels 30a and contacts the exposed surfaces, the method may include conducting repeated measurements to determine the identity and amount of gas or liquid within the plume. By conducting such repeated measurements, a change in mole amounts with time of each gas or liquid present in the plume may be determined.

With the change in mole amounts with time determined, the determined mole amount of each identified gas solubilized or liquid mixed in the plume may be extrapolated back in time to the instance of perforation to determine the amount of each gas solubilized or liquid in the plume at the instance of perforation. For example and without limitation, after perforating casing 12 in first interval 10a, at least a portion of the wellbore fluid 9 may be drawn into first interval 10a, such that the total amount of gas and liquid in the first plume increases or decreases with time. The method may include repeating the determining of the identity and amount of the gas or liquid in the first plume to determine a rate of change in the total amount of the gas or liquid contained in the first plume with time. The method may then include extrapolating the total amount of the gas or liquid contained in the first plume back in time to the instance of perforation based on the determined rate of change to determine the total amount of gas or liquid in the first plume at the time of perforation. The method may then include calculating the total amount of the gas or liquid within the first plume at the time of perforation to determine the concentration of the gas, both free and absorbed, or liquid within first interval 10a of low permeability formation 10.

In some embodiments, after measuring the concentration of gases or liquid in the first plume, the contents of the plume may be pumped back, i.e., reinjected, into the perforated interval by displacing the plume formed by the perforation into, for instance, first interval 10a. Displacing the plume formed by the perforation into the interval may include active pumping, for example, by using surface pumps, of additional fluid into wellbore 1 to force the gas or liquid back into the originating interval or another interval.

In certain embodiments, zonal isolation may be used to associate identity and amount of gases and liquid with particular intervals of the low permeability formation. FIGS. 1A, 1B, 1C depict an embodiment of zonal isolation. After perforation of first interval 10a, as shown in FIG. 1A, measurement of the identity and amount of gases and liquid of the first plume, and reinjection of the first plume into first interval 10a, first interval 10a may be isolated from second interval 10b. Following isolation of first interval 10a from interval 10b, second interval 10b may be perforated, a second plume formed, and the identity and amount of gases and liquid of the second plume determined. This process may be repeated for multiple intervals. The use of zonal isolation may assist in determining the location of particular gases and liquid and the amounts associated therewith.

FIG. 1B illustrates an embodiment of zonal isolation using a bridge plug. First interval 10a may be isolated from second interval 10b by setting bridge plug 27a between interval 10a and interval 10b. The bridge plug may be a permanent or retrievable bridge plug. Following isolation of first interval 10a from interval 10b, casing 12 may be perforated as described above to form perforation tunnels 30b in second interval 10b to fluidly couple second interval 10b of shale reservoir 10 to wellbore 1. A second plume may be formed, and the identity and amount of gases and liquid in the second plume may be determined.

FIG. 1C further illustrates zonal isolation through use of a bridge plug. After determination of the identity and amount of gases and liquid in the second plume, the second plume may be reinjected into second interval 10b, and as shown in FIG. 1C, bridge plug 27b inserted so as to isolate second interval 10b from third interval 10c. Following isolation of second interval 10b from third interval 10c, casing 12 may be perforated as described above to form perforation tunnels 30c in third interval 10c to fluidly couple third interval 10c of low permeability formation 10 to wellbore 1. A third plume may be formed, and the identity and amount of gases and liquid in the third plume may be determined. In some embodiments, each successive interval that is perforated is located at a shallower depth than the prior perforated interval.

In certain embodiments of the present disclosure, an inflatable or swellable packer may be used in place of a bridge plug. In yet other embodiments, a straddle packer may be used to isolate a particular interval.

In other embodiments, perforation and determination of identity and amount of gases and liquid may be performed upon penetration of an interval, prior to intersection with lower intervals. For example and without limitation, wellbore 1 may be drilled, cased, and cemented until wellbore 1 intersects third interval 10c, but does not intersect second interval 10b or first interval 10a. In such embodiments, the method may include perforating third interval 10c of casing 12 in wellbore 1 to fluidly couple third interval 10c of low permeability formation 10. A first plume may be formed and determination of the identity and amount of gases and liquid made. This process may be repeated with respect to second interval 10b to form a second plume and first interval 10a to form a third plume.

In certain embodiments of the present disclosure, reinjection of the first, second, and/or third plumes may be omitted.

In certain embodiments wherein zonal isolation is used, determination may be made as to which interval of shale reservoir 10 has a greater concentration of total free and absorbed gas or liquid contained therein. For example and without limitation, the method may include determining which of first interval 10a, section interval 10b, or third interval 10c has the greater concentration of total free and absorbed desired gas or liquid contained therein. Evaluating each interval 10a, 10b and 10c of low permeability formation 10 allows an interval having the greatest amount of the most desired gas thereof to be identified.

The method may include extracting the gas from the interval of low permeability formation 10 that is determined to have the greater concentration of total free and absorbed gas or liquids contained therein. Extraction of the gas or liquid may be performed by methods well known to those skilled in the art, such as directional drilling or fracturing.

In certain embodiments, the amount of the solubilized gas, liquid hydrocarbons, or combinations thereof within the plume may be calculated by lowering a chemical concentration measurement device into the plume to multiple discrete depths in the plume. The chemical concentration at each of the multiple discrete depths may be measured, with each measurement forming a signal. Each signal may be processed to determine an identity and amount of the solubilized gas, liquid, or combinations thereof at each of the multiple discrete depths within the plume. In some of these embodiments, the determined amount of the solubilized gas, liquid, or combinations thereof within the plume may be integrated as a function of depth to determine an amount of solubilized gas, liquid, or combinations thereof in the plume.

In other embodiments, the amount of the solubilized gas, liquid, or combinations thereof within the plume can be calculated by providing a chemical concentration measurement device where the chemical concentration measurement device is located at a wellhead. The chemical concentration measurement device may be in fluid communication with the wellbore fluid. The plume may then be circulated such that the plume reaches the wellhead. The chemical concentration of the plume may be measured and a signal formed. The signal may then be processed to determine an identity and amount of the solubilized gas, liquid, or combinations thereof within the plume.

Examples of chemical concentration measurement devices include, but are not limited to Laser Induced. Breakdown Spectroscopy (LIBS), intracavity laser spectroscopy, biosensor/dissolved O2 sensor that may use 02 consumption as a proxy for CH4 concentration, photoacoustic spectroscopy, amperometry/electrochemical detection, Surface Enhanced Raman Spectroscopy (SERS), evanescent wave spectroscopy, Surface Plasmon Resonance Spectroscopy (SPR), METS-CAPSUM, HydroC/CH4, deep-sea methane sensor, deep-sea gas analyzer, equilibrator, in-situ mass spectrometer, biosensor, FENN'S, and fiber optic chemical sensors.

In other embodiments, the concentration of an inorganic chemical in the low permeability formation may be determined prior to perforating the interval. In some embodiments, the inorganic chemical released by the pulverized rock could include uranium, thorium or potassium salts. The volume of rock pulverized by the perforating process may be determined by comparing the total amounts of inorganic chemical present in the plume with concentration logs for these same compounds derived from Petrophysical logs, such as spectral gamma ray SGR. These logs may be acquired prior to perforating the interval, and would yield the amount of inorganic chemical present in the interval per unit (e.g. moles/m3). For example, if the amount of uranium present in the plume is 0.1 mole, and Petrophysical analysis of SGR logs indicates that the concentration of uranium in the rock prior to perforating was 2 mole/m3, then the volume of rock that was pulverized by the perforating process is 0.1/2=0.05 m3.

EXAMPLES

The disclosure having been generally described, the following examples show particular embodiments of the disclosure. It is understood that the example is given by way of illustration and is not intended to limit the specification or the claims. All compositions percentages given in the examples are by weight.

Example 1

A sample of methane in water was formed by dissolving methane at a known concentration in water. The process was twice repeated for different known methane concentrations.

Figure 2:
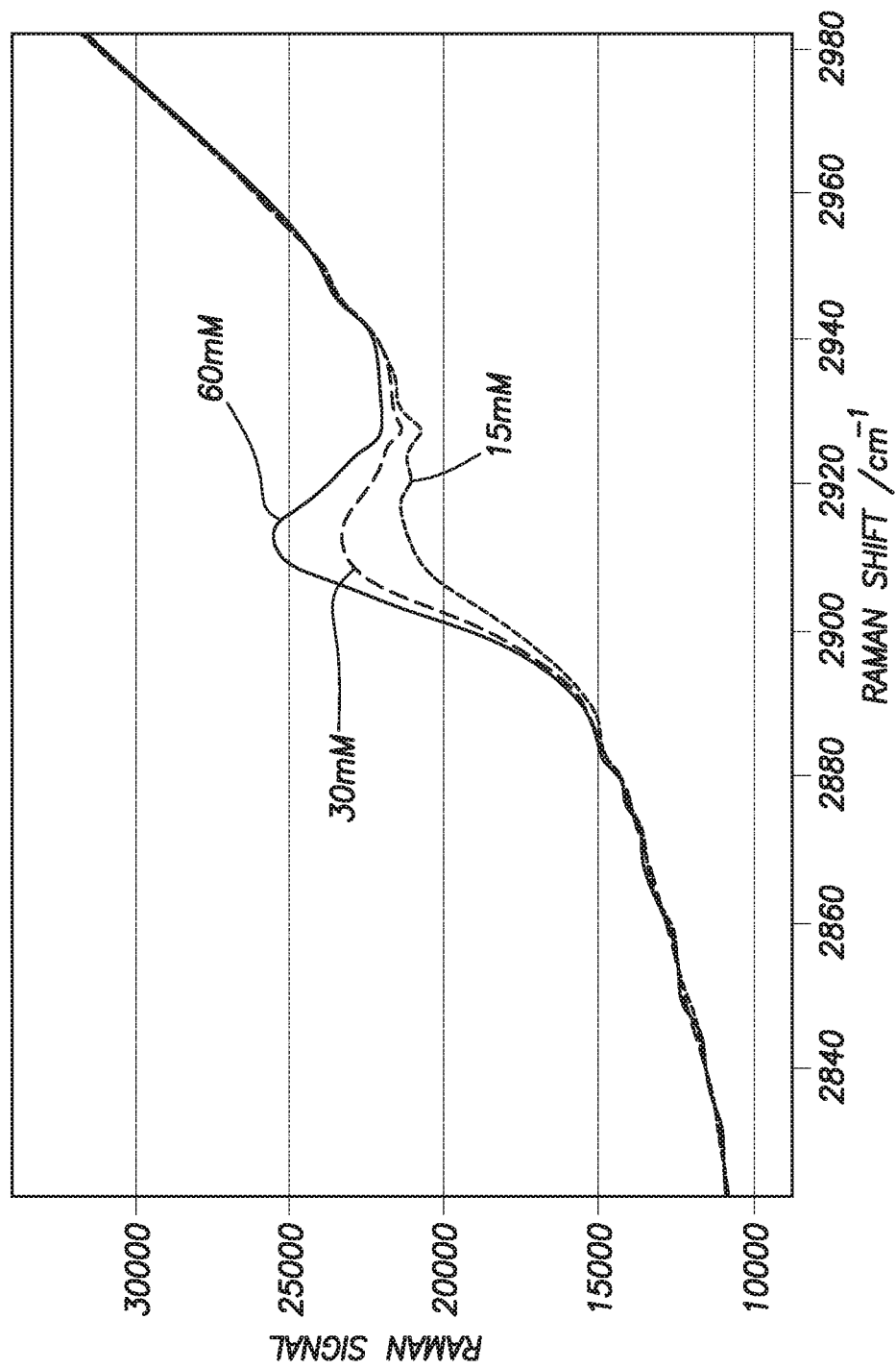
FIG. 2 is a graph of a spectral signature for methane at three different concentrations in accordance with Example 1.

FIG. 2 shows a graph of a Raman spectral signature for methane dissolved in water at the three different concentrations.

Example 2

A Raman spectrometer is converted to make a conversion between a Raman spectrum and methane partial pressure. This is done by one of two methods. Both involve preparing samples of methane in equilibrium with water at various pressures. Raman spectra of the samples are taken. The pressures of the samples should correlate with the range of methane partial pressures expected in the unknown samples.

The concentration of methane in each sample's fluid can be calculated by Henry's law, using an appropriate Henry's law constant for the given conditions, i.e. temperature, salinity and methane partial pressure, or by some other method that indicates the solubility of methane in water. This methane in fluid concentration can then be correlated with the intensity of the methane peak in the Raman spectra of the sample. This method is robust and has several advantages.

Alternately, the partial pressure of methane can also be directly correlated with the intensity of the methane peak in the Raman spectra.

With the above correlations, either methane concentration or partial pressure can be calculated by measuring the Raman spectrum of an unknown sample. Correlating directly to partial pressure, while simpler, introduces a larger possibility for error, as the unknown fluid may not have the same relationship between dissolved methane and partial pressure, i.e. Henry's law constant (or other solubility relationship). Conversely, correlating to concentration and then to partial pressure provides the advantage that the relationship between concentration and Raman signal will not be affected by differences in the fluid quality, without it being obvious in the Raman spectra, example: an unknown peak in the same spectral range as the methane. Subsequent conversion of methane concentration to partial pressure uses Henry's law and a Henry's law constant that is corrected for the unknown sample's temperature and salinity, which can be measured in a wellbore, for example. In both of these methods the partial pressure of methane is calculated. This then allows a direct reading from the isotherm to determine the gas content.

Many factors such as localized depressurization may be taken into account when determining the partial pressure.

Another example of the steps to determine the partial pressure based upon an optical measurement of the methane concentration to reach partial pressure is as follows. First, construct a calibration of Raman or other spectrometer counts that relates those counts to methane concentration dissolved in water (preferably, an ideal water such as deionized water). This requires that one first apply a methane partial pressure at a room temperature and allow the system to come to equilibrium; preferably this is done for a pressure range that exceeds the range of interest in the well. Then, one measures the Raman signal from the methane in the ideal water sample and calculates the methane concentration dissolved in that sample. Then, one can correlate this concentration with the methane partial pressure that was applied, using a Henry's law constant for water at room temperature. This gives a calibration between Raman signal, concentration in the water and partial pressure of methane above the water at room temperature.

The function is:
moles of $CH_4$/moles of water'" Pressure[atm]*Henry's constant [mM]$CH_4$=Pressure [atm]*Henry's contant*:35 moles of water/liter water*1000

Figure 3:
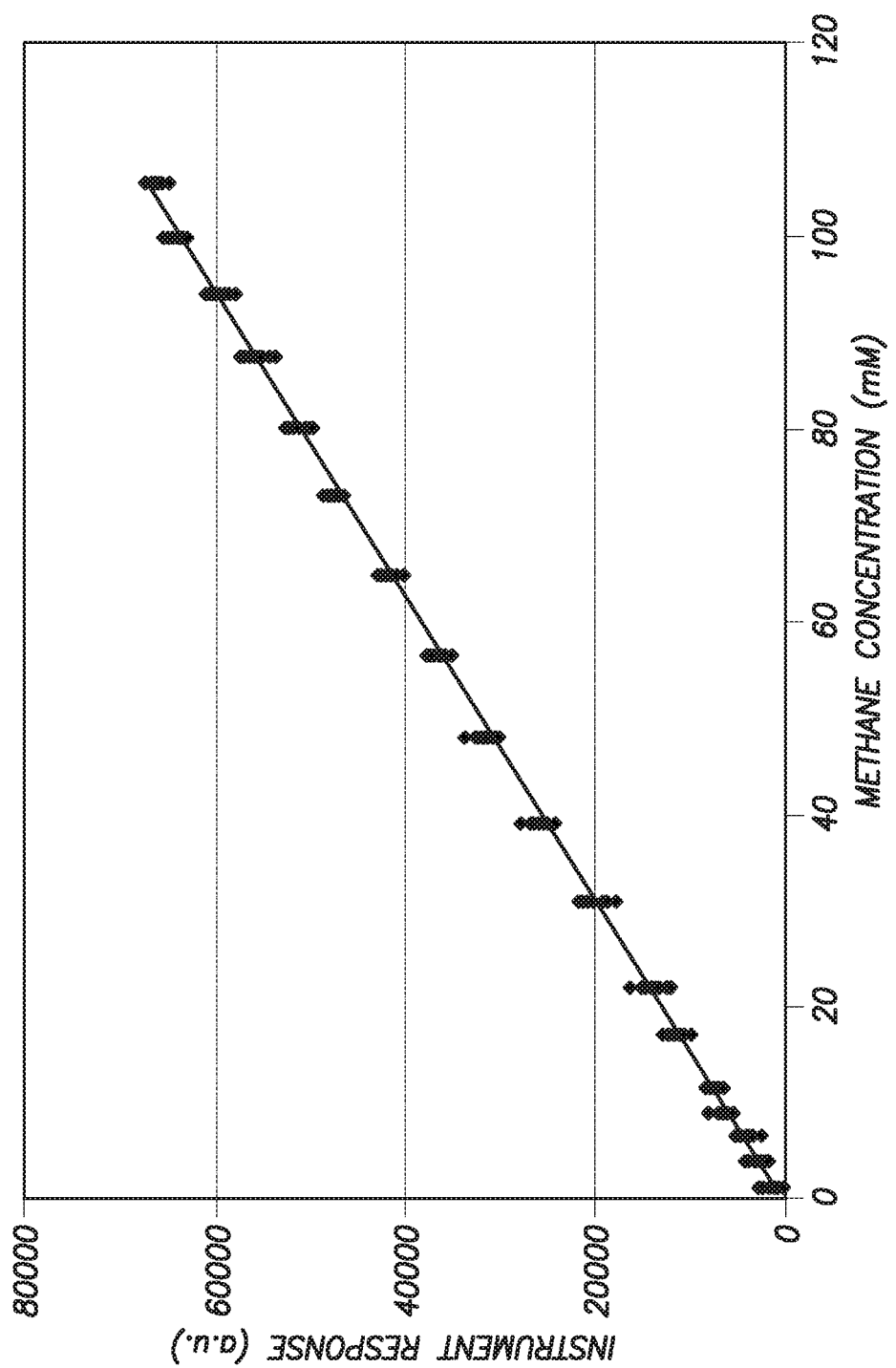
FIG. 3 is a graph of a calibration of signal to methane concentration in accordance with Example 2.

FIG. 3 depicts an example of a calibration curve for Raman signal responses to methane dissolved in water.

Example 3

Figure 4:
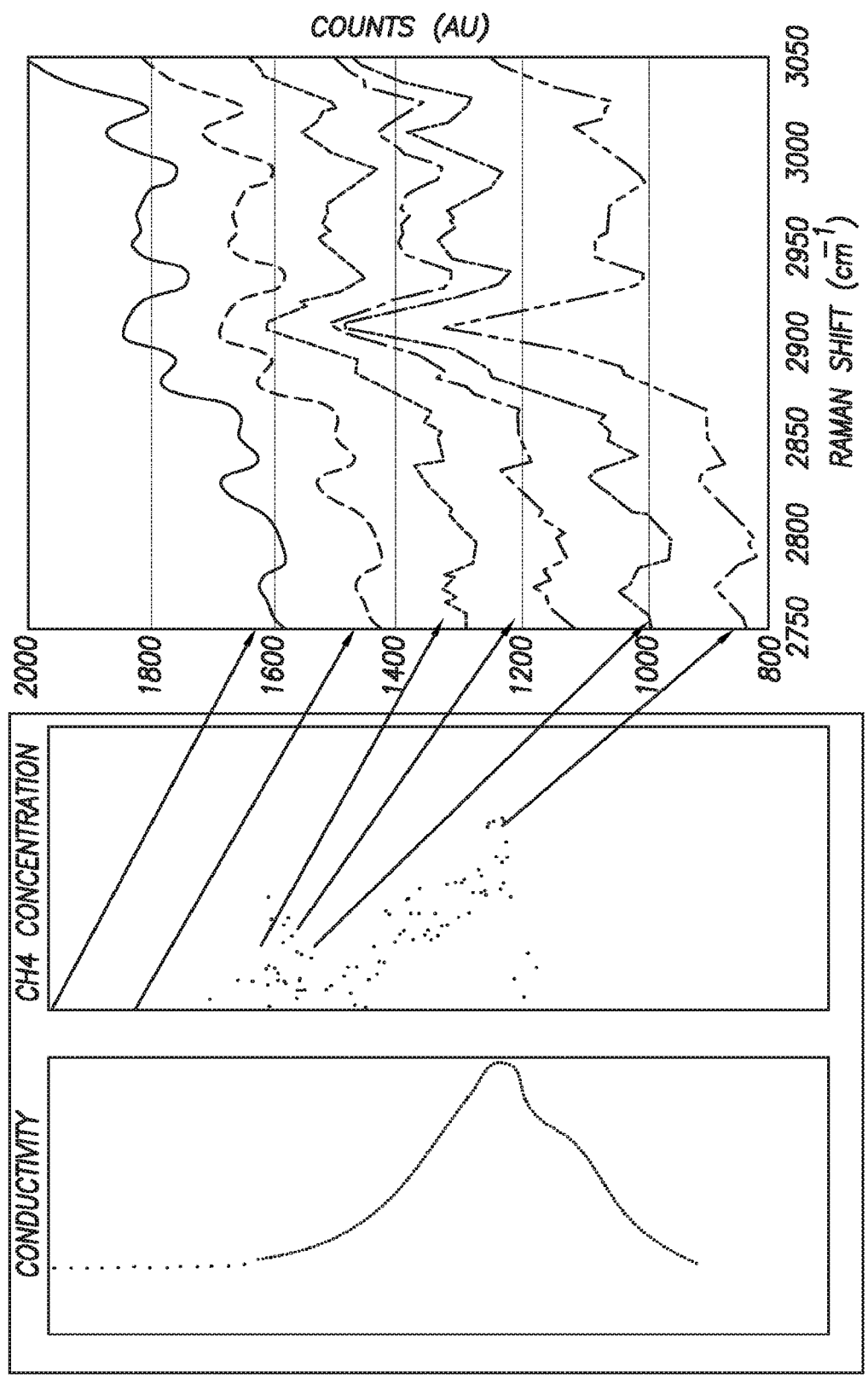
FIG. 4 is a representation of a wellbore with plume gas concentrations plotted in accordance with Example 3.

A well was drilled and cased through a shale formation and then perforated at a depth across the shale interval as described previously. A logging toolstring incorporating a Raman spectrometer of type 250 shown in FIG. 7, as well as pressure, temperature and conductivity sensors, was deployed on wireline at 30 feet per minute to the top of the plume created by the perforating process. The logging speed was then slowed to five per minute down through the plume, with Raman spectra, pressure, temperature and conductivity measurements obtained at 1 second intervals. FIG. 4 depicts an example of a plot of the concentration of methane versus depth.

Example 4

A well was drilled through multiple formations, and analyzed with a suite of open hole logging instruments to determine various geochemical and petro-physical properties of the well. The well was then cased and cemented. The well had three separate gas shale formations in need of analysis for gas composition and gas content in order to determine which of the three shale formations had the greatest production potential for subsequent development through drilling of a horizontal lateral borehole. Testing of the three shale formations was conducted using the steps set forth in Table 2.

TABLE 2

| Step | Procedure |
|---|---|
| 1 | Hold safety meeting. Review JSAs. |
| 2 | MIRU coil tubing unit. |
| 3 | Nipple up and test coil tubing BOPs, injector, and flowback iron. |
| 4 | Make up coil tubing displacement BHA per attachment. Pull test to 10,000 lbs and pressure test to 2500 psi. |
| 5 | RIH with coil tubing to PBTD. Casing tally is unavailable for this well, but the float collar should be around 6100'. |
| 6 | Circulate entire well to fresh water. This should take approximately 137 bbls surface to surface, but pump until the returns are clean. |
| 7 | Blow down CT with N2 while pulling out of the hole, as long as the well is kept full. Alternatively, blow down after well is shut in. |
| 8 | POOH with coil tubing. Rig down coil tubing unit, leaving the pump. |
| 9 | MIRU wireline unit. |
| 10 | Rig up coil tubing pump to be able to pump into the well. |
| 11 | Make up wireline BHA #1 (pelf guns) |
| 12 | Pull wireline BHA into lubricator and make up to lower master valve. Test lubricator and connection tp 2000 psi. |
| 13 | RIH with wireline to so that the 10' of guns are across 6042'-6052' targeting Shale 1. |
| 14 | Correlate depth to Shale 1 and fire guns. If casing collar is encountered, perforate anyway. |
| 15 | POOH with wireline. |
| 16 | Make up wireline BHA #2 (Welldog tool). Pull into lubricator, stab onto upper master valve, and test. |
| 17 | RIH with Welldog tool per Welldog dedicated run procedure. |
| 18 | Log across Shale 1 per Welldog dedicated run procedure. |
| 19 | POOH with Welldog tool. |
| 20 | Make up wireline BHA #3 (Welldog water sampling tool). RIH and collect water sample at depth per Welldog procedure. POOH. |
| 21 | Bullhead 2-3 bbls fresh water into the well with the coil tubing pump. This will displace the 100' or so of contaminated water above the previous perforations into formation and spot clean fresh water across the next test interval in Shale 2 |
| 22 | Make up and RIH with wireline BHA #4 (CIBP and pelf guns) to set the CIBP 10' above the previous perforations, maintaining pressure on the well. |
| 23 | Set the CIBP. Once the CIBP is set, pressure may be bled off of the well. |
| 24 | Pull up so that the 10' of guns are from 6007' to 6017' in Shale 2 and fire guns. POOH with wireline. |
| 25 | Make up wireline BHA #5 (Welldog tool). |
| 26 | RIH and log Shale 2 per Welldog dedicated procedure. POOH wireline BHA #5. |
| 27 | Make up wireline BHA #6 (Welldog water sampling tool). RIH and collect water sample at depth per Welldog procedure. POOH. |
| 28 | Bullhead 2-3 bbls fresh water into the well with the coil tubing pump. This will displace the 100' or so of contaminated water above the previous perforations into formation and spot clean fresh water across the final test interval in Shale 3. |
| 29 | Make up and RIH with wireline BHA #7 (CIBP and pelf guns) to set the CIBP 10' above the previous perforations, maintaining pressure on the well. |
| 30 | Set the CIBP. Once the CIBP is set, pressure may be bled off of the well. |
| 31 | Pull up so that the 10' of guns are from 5957' to 5967' in the Shale 3 and fire guns. POOH with wireline. |
| 32 | Make up wireline BHA #8 (Welldog tool). |
| 33 | RIH and log Shale 3 per Welldog dedicated procedure. POOH wireline BHA #8. |
| 34 | Make up wireline BHA #9 (Welldog water sampling tool). RIH and collect water sample at depth per Welldog procedure. POOH. |
| 35 | Make up wireline BHA #10 (CIBP). |
| 36 | RIH and set CIBP 50' above top perfs (approx. 5900'). Bleed off and perform negative pressure test. |
| 37 | POOH. Nipple down all. Remove lower master valve and replace cap. |

Depending on the context, all references herein to the "disclosure" may in some cases refer to certain specific embodiments only. In other cases it may refer to subject matter recited in one or more, but not necessarily all, of the claims. While the foregoing is directed to embodiments, versions and examples of the present disclosure, which are included to enable a person of ordinary skill in the art to make and use the disclosures when the information in this patent is combined with available information and technology, the disclosures are not limited to only these particular embodiments, versions and examples. Other and further embodiments, versions and examples of the disclosure may be devised without departing from the basic scope thereof and the scope thereof is determined by the claims that follow.

What is claimed is:

1. A method comprising:
    drilling a wellbore, the wellbore intersecting a low permeability formation at an interval of the formation, the wellbore having a vertical section, a deviated section, a lateral section, or a combination thereof;
    perforating the wellbore at the interval to fluidly couple the interval and the wellbore;
    liberating free and absorbed gas, liquid, or a combination thereof entrapped within the interval;
    forming a plume comprising solubilized gas, liquid, or a combination thereof by solubilizing in the wellbore fluid the free and absorbed gas, mixing the liquid with the wellbore fluid, or a combination thereof; and
    calculating an identity of gas, liquid, or combinations thereof in the plume;
    wherein after the step of calculating an identity of gas, liquid, or combinations thereof in the plume:
    calculating the amount of the solubilized gas, liquid, or combinations thereof within the plume to determine a concentration of the gas, liquid, or combinations thereof within the interval,
    wherein the step of calculating the amount of the solubilized gas, liquid, or combinations thereof within the plume comprises:
    providing a chemical concentration measurement device, the chemical concentration measurement device located at a wellhead, the chemical concentration measurement device in fluid communication with the wellbore fluid;
    circulating the plume such that the plume reaches the wellhead; and
    measuring a chemical concentration of the plume, the measurement forming a signal,
    processing the signal to determine an identity and amount of the solubilized gas, liquid, or combinations thereof within the plume.

2. The method of claim 1, wherein the interval is cased.

3. The method of claim 1, wherein the interval is uncased.

4. The method of claim 1, wherein the step of perforating the wellbore is performed on the vertical section, the deviated section, or the lateral section of the wellbore.

5. The method of claim 1, wherein the solubilized gas within the plume comprises methane.

6. The method of claim 1, further comprising determining a variation in the identity and amount of the gas, liquid, or a combination thereof within the plume by depth, by time, or by depth and by time.

7. The method of claim 1, wherein the wellbore fluid is comprised of water.

8. The method of claim 7, wherein the water is from the perforated interval, residual from drilling operations, residual from completion operations, or water added from a surface source.

9. The method of claim 1, wherein the step of calculating the amount of the solubilized gas, liquid, or combinations thereof within the plume comprises:
    (i) lowering a chemical concentration measurement device into the plume to multiple discrete depths in the plume;
    (ii) measuring a chemical concentration at each of the multiple discrete depths, each measurement forming a signal,
    (iii) processing each signal to determine an identity and amount of the solubilized gas, mixed liquid, or combinations thereof at each of the multiple discrete depths within the plume; and
    (iv) integrating the determined amount of the solubilized gas, liquid, or combinations thereof within the plume as a function of depth to determine an amount of solubilized gas, liquid, or combinations thereof in the plume.

10. A method comprising:
    drilling a wellbore, the wellbore intersecting a low permeability formation at an interval of the formation, the wellbore having a vertical section, a deviated section, a lateral section, or a combination thereof;
    perforating the wellbore at the interval to fluidly couple the interval and the wellbore;
    liberating free and absorbed gas, liquid, or a combination thereof entrapped within the interval;
    forming a plume comprising solubilized gas, liquid, or a combination thereof by solubilizing in the wellbore fluid the free and absorbed gas, mixing the liquid with the wellbore fluid, or a combination thereof; and
    calculating an identity of gas, liquid, or combinations thereof in the plume;
    determining the concentration of an inorganic chemical in the low permeability formation prior to the step of perforating the interval;
    measuring the concentration of the inorganic chemical in the plume; and
    determining the volume of the low permeability formation perforated.

11. The method of claim 10, wherein the inorganic chemical is a uranium, thorium, or potassium salt.

12. A method comprising:
    drilling a wellbore, the wellbore intersecting a low permeability formation at an interval of the formation, the wellbore having a vertical section, a deviated section, a lateral section, or a combination thereof;
    perforating the wellbore at the interval to fluidly couple the interval and the wellbore;
    liberating free and absorbed gas, liquid, or a combination thereof entrapped within the interval;
    forming a plume comprising solubilized gas, liquid, or a combination thereof by solubilizing in the wellbore fluid the free and absorbed gas, mixing the liquid with the wellbore fluid, or a combination thereof; and
    calculating an identity of gas, liquid, or combinations thereof in the plume;
    wherein the step of calculating the amount of the solubilized gas, liquid, or combinations thereof within the plume comprises:
    providing a chemical concentration measurement device, the chemical concentration measurement device located at a wellhead, the chemical concentration measurement device in fluid communication with the wellbore fluid;

circulating the plume such that the plume reaches the wellhead; and measuring a chemical concentration of the plume, the measurement forming a signal, processing the signal to determine an identity and amount of the solubilized gas, liquid, or combinations thereof within the plume;

wherein the step of calculating the amount of the solubilized gas, liquid, or combinations thereof within the plume comprises:

(i) providing incident radiation from a radiation source to the solubilized gas, liquid, or combinations thereof within the plume at multiple discrete depths in the plume, wherein interaction of the incident radiation with the solubilized gas, liquid, or combinations thereof within the plume forms characteristic radiation from the solubilized gas, liquid, or combinations thereof within the plume;

(ii) detecting the characteristic radiation with a radiation detector for each of the multiple discrete depths, wherein the radiation detector forms a signal representative of the characteristic radiation, wherein the steps of providing incident radiation from a radiation source at multiple discrete depths in the plume and detecting the characteristic radiation with a radiation detector for each of the multiple discrete depths forms a logging run;

(iii) processing each signal to determine an identity and amount of the solubilized gas, liquid, or combinations thereof at each of the multiple discrete depths within the plume; and (iv) integrating the determined amount of the solubilized gas, liquid, or combinations thereof within the plume as a function of depth to determine an amount of solubilized gas, liquid, or combinations thereof in the plume;

wherein processing each signal to determine the identity and amount of the solubilized gas, liquid, or combinations thereof at each of the multiple discrete depths within the plume comprises correlating each signal with a calibration function, wherein the calibration function is a function of signal versus amount of solubilized gas, liquid, or combinations thereof.

13. The method of claim 12, wherein, after perforating the first interval:

repeating steps (i)-(iv) to determine a rate of change in the total amount of the solubilized gas, liquid, or combinations thereof contained in the first plume with time;

extrapolating the total amount of the solubilized gas, liquid, or combinations thereof contained in the plume to the instance of perforation based on the determined rate of change to determine the total amount of solubilized gas, liquid, or combinations thereof in the plume at the time of perforation; and calculating the total amount of the solubilized gas, liquid, or combinations thereof within the plume at the time of perforation to determine the concentration of the gas, both free and absorbed, within the interval.

14. The method of claim 12, wherein a spectrometer comprises the radiation source and the radiation detector.

15. The method of claim 14, wherein the spectrometer is an optical spectrometer.

16. The method of claim 15, wherein the optical spectrometer is a Raman spectrometer, a near IR spectrometer, a IR spectrometer, a UV/Vis spectrometer or fluorimeter.

17. The method of claim 14, wherein the spectrometer is a mass spectrometer.

18. The method of claim 12, wherein the radiation detector is a membrane-coated semiconductor sensor.

19. The method of claim 12, wherein the step of processing the amount of the solubilized gas within the first plume to determine a concentration of the gas within the interval comprises:

determining the total mole amount of gas detected in the plume during a first logging run in accordance with the equation:

$$N_i = \sum_{x=1}^{Y} \frac{(C_{x+1} + C_x)(D_{x+1} - D_x)}{2}$$

wherein $N_i$ is the total amount of gas detected in the plume during the first logging run, D is a measurement depth, C is a measured gas concentration, x is a sample number; and Y is the total number of discrete samples acquired in the plume;

determining the total mole amount of gas released at the time of perforating in accordance with the equation:

$$N_0 = N_i - \frac{(N_l - N_i)}{dt} \Delta T$$

wherein $N_0$ is the total amount of gas released at the time of perforating, $N_1$ is the methane mole amount computed from a final logging run through the plume, dt is the time duration between the first and final logging run through the plume, and $\Delta T$ is the time duration between the instance of perforating and the first logging run through the plume;

converting the total gas amount released at the time of perforating to a volume of gas using the equation:

$$V_s = \frac{N_0 * R * T_s}{P_s}$$

wherein Vs is the volume of the solubilized gas within the plume, R is the universal gas constant, 0.08206 L·atm$^{-1}$·mol$^{-1}$·K$^{-1}$; $T_s$ is standard temperature, 288.71 K; and $P_s$ is standard pressure, 1 atmosphere;

equating the total volume of solubilized gas in the plume to the free and absorbed gas content for the shale interval using the equation:

$$G_c = \frac{K * V_s}{\rho * V_t}$$

wherein $V_s$ is the volume of the solubilized gas within the plume, $G_c$ is the amount in ft$^3$/short ton of the free and absorbed gas within the interval, K is a constant equal to 2000 lb/short ton, $\rho$ is the density in lb/ft$^3$ of shale in the interval, and $V_t$ is the total volume of shale pulverized from perforating the casing at the interval and is determined in accordance with the following equation:

$$V_t = H * spf * \frac{\pi}{4} d^2 * L$$

wherein H is the total length in feet of a perforating gun used in the perforating, spf is the shot density used in the perforating, d is the perforation tunnel diameter in feet, and L is the perforation tunnel length in feet.

20. The method of claim 12, further comprising measuring pressure, conductivity, temperature, or combinations thereof at each of the multiple discrete depths within the first plume.

21. A method comprising:
drilling a wellbore, the wellbore intersecting a low permeability formation at an interval of the formation, the wellbore having a vertical section, a deviated section, a lateral section, or a combination thereof;
perforating the wellbore at the interval to fluidly couple the interval and the wellbore;
liberating free and absorbed gas, liquid, or a combination thereof entrapped within the interval;
forming a plume comprising solubilized gas, liquid, or a combination thereof by solubilizing in the wellbore fluid the free and absorbed gas, mixing the liquid with the wellbore fluid, or a combination thereof; and
calculating an identity of gas, liquid, or combinations thereof in the plume;
after the step of determining an identity and amount of solubilized gas, liquid, or combinations thereof in the plume:
reinjecting the solubilized gas into the interval.

\* \* \* \* \*